(12) United States Patent
Ghebre-Sellassie et al.

(10) Patent No.: US 9,770,514 B2
(45) Date of Patent: Sep. 26, 2017

(54) TAMPER-RESISTANT PHARMACEUTICAL DOSAGE FORMS

(71) Applicant: ExxPharma Therapeutics LLC, Somerville, NJ (US)

(72) Inventors: Isaac Ghebre-Sellassie, Morris Plains, NJ (US); Hibreniguss Terefe, Piscataway, NJ (US)

(73) Assignee: ExxPharma Therapeutics LLC, Somerville, NJ (US)

( * ) Notice: Subject to any disclaimer, the term of this patent is extended or adjusted under 35 U.S.C. 154(b) by 25 days.

(21) Appl. No.: 14/157,658

(22) Filed: Jan. 17, 2014

(65) Prior Publication Data

US 2015/0064250 A1    Mar. 5, 2015

Related U.S. Application Data

(60) Provisional application No. 61/959,830, filed on Sep. 30, 2013.

(51) Int. Cl.
| | |
|---|---|
| *A61K 9/26* | (2006.01) |
| *A61K 47/48* | (2006.01) |
| *A61K 31/138* | (2006.01) |
| *A61K 31/485* | (2006.01) |
| *A61K 9/20* | (2006.01) |
| *A61K 31/137* | (2006.01) |

(52) U.S. Cl.
CPC ...... *A61K 47/48184* (2013.01); *A61K 9/2009* (2013.01); *A61K 9/2027* (2013.01); *A61K 9/2054* (2013.01); *A61K 9/2077* (2013.01); *A61K 31/137* (2013.01); *A61K 31/138* (2013.01); *A61K 31/485* (2013.01)

(58) Field of Classification Search
CPC ...... A61K 9/20; A61K 9/2004; A61K 9/2013; A61K 9/2022; A61K 9/2027; A61K 9/205
USPC ................................................ 424/465–489
See application file for complete search history.

(56) References Cited

U.S. PATENT DOCUMENTS

| | | |
|---|---|---|
| 7,157,103 B2 | 1/2007 | Sackler |
| 7,332,182 B2 | 2/2008 | Sackler |
| 7,399,488 B2 | 7/2008 | Hirsh et al. |
| 7,510,726 B2 | 3/2009 | Kumar et al. |
| 7,511,054 B2 | 3/2009 | Stinchcomb et al. |
| 7,658,939 B2 | 2/2010 | Oshlack et al. |
| 7,682,632 B2 | 3/2010 | Oshlack et al. |
| 7,718,192 B2 | 5/2010 | Oshlack et al. |
| 7,727,557 B2 | 6/2010 | Sackler |
| 7,771,707 B2 | 8/2010 | Hirsh et al. |
| 7,776,314 B2 | 8/2010 | Bartholomaus et al. |
| 7,790,215 B2 | 9/2010 | Sackler et al. |
| 7,842,307 B2 | 11/2010 | Oshlack et al. |
| 7,842,309 B2 | 11/2010 | Oshlack et al. |
| 7,842,311 B2 | 11/2010 | Oshlack et al. |
| 7,955,619 B2 | 6/2011 | Shah et al. |
| 8,017,148 B2 | 9/2011 | Sackler |
| 8,075,872 B2 | 12/2011 | Arkenau-Maric et al. |
| 8,097,278 B2 | 1/2012 | Sackler |
| 8,101,630 B2 | 1/2012 | Kumar et al. |
| 8,124,126 B2 | 2/2012 | Bosse et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,158,156 B2 | 4/2012 | Matthews et al. |
| 8,168,217 B2 | 5/2012 | Yum et al. |
| 8,211,905 B1 | 7/2012 | King et al. |
| 8,236,351 B2 | 8/2012 | Oshlack et al. |
| 8,252,328 B2 | 8/2012 | Tzannis et al. |
| 8,252,329 B2 | 8/2012 | Tzannis et al. |
| 8,273,798 B2 | 9/2012 | Bausch et al. |
| 8,298,579 B2 | 10/2012 | Abreu |
| 8,309,568 B2 | 11/2012 | Stinchcomb et al. |
| 8,323,889 B2 | 12/2012 | Arkenau-Maric et al. |
| 8,329,720 B1 | 12/2012 | King et al. |
| 8,337,888 B2 | 12/2012 | Wright et al. |
| 8,338,444 B1 | 12/2012 | King et al. |
| 8,349,362 B2 | 1/2013 | Soscia et al. |
| 8,354,124 B2 | 1/2013 | Yum et al. |
| 8,357,399 B2 | 1/2013 | Oshlack et al. |
| 8,362,029 B2 | 1/2013 | Evenstad et al. |
| 8,367,693 B1 | 2/2013 | King et al. |
| 8,372,432 B2 | 2/2013 | Han et al. |
| 8,377,453 B2 | 2/2013 | Han et al. |
| 8,383,152 B2 | 2/2013 | Jans et al. |
| 8,389,007 B2 | 3/2013 | Wright et al. |
| 8,394,408 B2 | 3/2013 | Han et al. |
| 8,409,616 B2 | 4/2013 | Kumar et al. |
| 8,415,401 B2 | 4/2013 | Yum et al. |
| 8,420,056 B2 | 4/2013 | Arkenau-Maric et al. |
| 8,420,120 B2 | 4/2013 | Yum et al. |
| 8,420,700 B1 | 4/2013 | Bausch et al. |
| 8,425,933 B2 | 4/2013 | Mehta |
| 8,445,018 B2 | 5/2013 | Habib et al. |
| 8,449,909 B2 | 5/2013 | Hirsh et al. |
| 8,460,640 B2 | 6/2013 | Vinson et al. |
| 8,461,137 B2 | 6/2013 | Mickle et al. |
| 8,465,774 B2 | 6/2013 | Breder et al. |

(Continued)

FOREIGN PATENT DOCUMENTS

| | | |
|---|---|---|
| EP | 0367746 A2 | 5/1990 |
| EP | 0294103 B1 | 1/1995 |

(Continued)

*Primary Examiner* — Micah-Paul Young
(74) *Attorney, Agent, or Firm* — Harvest IP Law LLP

(57) ABSTRACT

The invention provides a tamper-resistant dosage form including a therapeutic agent-substrate complex embedded in a thermo-formable matrix; such that the complex includes at least one therapeutic agent bound to at least one substrate to form the therapeutic agent-substrate complex. The at least one substrate is being selected from the group consisting of a polyelectrolyte, an organic counter-ion, a pharmacologically inert organic component of a prodrug, an inclusion compound and an inorganic adsorbent; and the thermo-formable matrix includes one or more thermoplastic polymers and optionally at least one pharmaceutical additive.

44 Claims, No Drawings

(56) References Cited

U.S. PATENT DOCUMENTS

| | | |
|---|---|---|
| 8,470,361 B2 | 6/2013 | Pettersson |
| 8,476,291 B1 | 7/2013 | King et al. |
| 8,481,560 B2 | 7/2013 | Stinchcomb et al. |
| 8,486,448 B2 | 7/2013 | Rahmouni et al. |
| 8,486,449 B2 | 7/2013 | Rahmouni et al. |
| 8,491,935 B2 | 7/2013 | Mehta et al. |
| 8,501,160 B2 | 8/2013 | Cailly-Dufestel et al. |
| 8,512,759 B1 | 8/2013 | McMahen et al. |
| 8,518,443 B2 | 8/2013 | Breder et al. |
| 8,524,275 B2 | 9/2013 | Oshlack et al. |
| 8,529,948 B1 | 9/2013 | Wright et al. |
| 8,557,291 B2 | 10/2013 | Rariy et al. |
| 8,563,038 B2 | 10/2013 | Andersen et al. |
| 8,569,329 B1 | 10/2013 | King et al. |
| 8,569,330 B1 | 10/2013 | King et al. |
| 8,575,151 B1 | 11/2013 | Bristol et al. |
| 8,586,088 B2 | 11/2013 | Oshlack et al. |
| 8,586,575 B1 | 11/2013 | King et al. |
| 8,597,684 B2 | 12/2013 | Mehta et al. |
| 8,603,526 B2 | 12/2013 | Tygesen et al. |
| 8,623,412 B2 | 1/2014 | Farid et al. |
| 8,623,418 B2 | 1/2014 | Liang et al. |
| 2005/0175733 A1* | 8/2005 | Thorengaard ............ A23G 4/00 426/3 |
| 2007/0048228 A1* | 3/2007 | Arkenau-Maric ... A61K 9/2027 424/10.1 |
| 2008/0074669 A1* | 3/2008 | Dorrington ............ G01B 11/24 356/445 |
| 2008/0075770 A1 | 3/2008 | Vaughn et al. |
| 2011/0020451 A1 | 1/2011 | Bartholomaus et al. |
| 2012/0148672 A1 | 6/2012 | Mehta et al. |
| 2013/0005823 A1 | 1/2013 | Emigh et al. |
| 2013/0022646 A1 | 1/2013 | Rudnic et al. |
| 2013/0045960 A1 | 2/2013 | Hirsh et al. |
| 2013/0122087 A1 | 5/2013 | Habib et al. |
| 2013/0122101 A1 | 5/2013 | Habib et al. |
| 2013/0129825 A1 | 5/2013 | Billoet |
| 2013/0171257 A1 | 7/2013 | Kumar et al. |
| 2013/0217716 A1 | 8/2013 | Wright et al. |
| 2013/0280176 A1 | 10/2013 | Diezi et al. |
| 2013/0280177 A1 | 10/2013 | Raman et al. |
| 2013/0281480 A1 | 10/2013 | Yum et al. |
| 2013/0287845 A1 | 10/2013 | Yum et al. |
| 2013/0289062 A1 | 10/2013 | Kumar et al. |
| 2013/0295168 A1 | 11/2013 | Yum et al. |
| 2013/0295170 A1 | 11/2013 | Dordunoo |
| 2013/0310413 A1 | 11/2013 | Hirsh et al. |
| 2013/0337059 A1 | 12/2013 | Yum et al. |
| 2013/0337060 A1 | 12/2013 | Yum et al. |
| 2013/0338229 A1 | 12/2013 | King et al. |
| 2013/0344143 A1 | 12/2013 | Rosenberg et al. |
| 2014/0004191 A1 | 1/2014 | Rahmouni et al. |
| 2014/0010860 A1 | 1/2014 | Odidi et al. |
| 2014/0010873 A1 | 1/2014 | Tygesen et al. |
| 2014/0010874 A1 | 1/2014 | Sackler |
| 2014/0010875 A1 | 1/2014 | Huang |
| 2014/0011832 A1 | 1/2014 | Huang |
| 2014/0011842 A1 | 1/2014 | Scicinski et al. |
| 2014/0017310 A1 | 1/2014 | Gower et al. |

FOREIGN PATENT DOCUMENTS

| | | | |
|---|---|---|---|
| EP | 0565301 B1 | 2/1999 | |
| JP | EP 0294103 B1 * | 1/1995 | ........... A61K 9/5026 |
| WO | 9211871 A1 | 7/1992 | |
| WO | 9827961 A2 | 7/1998 | |
| WO | 2006106344 A2 | 10/2006 | |
| WO | 2012061779 A1 | 5/2012 | |
| WO | 2012112952 A1 | 8/2012 | |
| WO | 2013077851 A1 | 5/2013 | |
| WO | 2013128276 A2 | 9/2013 | |
| WO | 2013153451 A2 | 10/2013 | |
| WO | 2013158810 A1 | 10/2013 | |
| WO | 2013158814 A1 | 10/2013 | |
| WO | 2014006004 A1 | 1/2014 | |
| WO | 2014011830 A1 | 1/2014 | |

* cited by examiner

TAMPER-RESISTANT PHARMACEUTICAL DOSAGE FORMS

CROSS REFERENCE TO RELATED APPLICATION

This application is based on, and claims the benefit of U.S. Provisional Patent Application No. 61/959,830, filed Sep. 3, 2013, which is incorporated herein by reference.

FIELD OF THE INVENTION

The present invention relates to an improved pharmaceutical dosage form. More particularly, the invention relates to a tamper-resistant dosage form including a therapeutic agent-substrate complex, a thermoplastic polymer, and optionally, one or more pharmaceutical additives, and the method of making same.

BACKGROUND OF INVENTION

Product tampering occurs when a dosage form is manipulated to achieve an objective in ways that is not intended per dosing instructions. It may involve drug abusers who tamper the dosage form to obtain euphoria, or non-abusers such as patients and caregivers who innocently tamper with the dosage form to address legitimate concerns. For example, an elderly patient may break a dosage form to facilitate swallowing or a caregiver may break a dosage form to reduce the therapeutic dose.

While drug abuse has been common with all dosage forms, modified release products have been particularly attractive to drug abusers due to the high drug content in the dosage forms. When these dosage forms are tampered with or altered, they may lead to more rapid release of the therapeutic agent, which in turn may provide the drug abusers with greater euphoria that they desperately desire.

To address the drug abuse epidemic, pharmaceutical companies have started to develop abuse deterrent formulations, and the FDA has also issued a guideline related to the subject to encourage development of more effective tamper-resistant formulations. Abuse deterrent formulations are designed to thwart deliberate attempts by drug-abusers to extract the active ingredient or blunt the euphoric effects from unapproved methods of administration.

Common methods of drug abuse include: (1) oral ingestion, where the dosage form is chewed, crushed, milled or ground and swallowed, with or without co-ingestion of alcohol, to destroy the release controlling matrix and deliver high doses of therapeutic agent into the gastrointestinal tract; (2) intravenous injection, which involves extraction of the therapeutic agent from the dosage form using an appropriate solvent, followed by injection of the therapeutic agent directly into the blood stream; (3) nasal snorting, where the dosage form is crushed, milled, or ground into a fine powder and administered intra-nasally to facilitate rapid drug absorption through the lining of the nasal passages; and (4) smoking, where the therapeutic agent is vaporized for inhalation by subjecting the dosage form to heat.

In addition, dosage forms, particularly modified release dosage forms, are relatively large in size and may pose a dosing challenge to many people including the elderly and young. Often, patients and caregivers may break the dosage form to reduce the size. By doing so, they inadvertently compromise the release controlling mechanism of the dosage form and potentially lead to dose dumping, often with adverse consequences.

To circumvent dosage form tampering, many tamper resistant formulations have been described.

U.S. Pat. No. 7,510,726 describes a therapeutic pharmaceutical composition comprising a mixture consisting of at least one opioid analgesic, gel forming polyethylene oxide, and at least one disintegrant.

U.S. Pat. No. 7,771,707 describes a solid abuse deterrent pharmaceutical composition of a pharmaceutically active agent prone to abuse, and one or more fatty acids or fatty amines present in molar excess relative to the pharmaceutically active agent.

U.S. Pat. No. 7,776,314 describes parenteral abuse-proofed solid dosage form for oral administration, comprising one or more active ingredients with potential for abuse, and at least one viscosity-increasing agent.

U.S. Pat. No. 8,075,872 describes an abuse resistant dosage form thermoformed by extrusion and having a breaking strength of at least 500 N, which contains a mixture of one or more active ingredients with abuse potential, polyalkylene oxides, physiologically acceptable auxiliary substances, and optionally wax and cellulosic derivatives.

U.S. Pat. No. 8,409,616 describes a therapeutic pharmaceutical composition comprising a water-soluble drug susceptible to abuse, a gel forming polymer and a disintegrant.

U.S. Pat. No. 8,449,909 describes a therapeutically effective pharmaceutical composition comprising solid microparticles, wherein the microparticles comprise an active agent, one or more fatty acids, and one or more carrier materials selected from waxes or wax-like substances.

U.S. Patent Application Publication 2008/0075770 describes a monolithic solidified oral dosage form prepared by a thermal process comprising a therapeutic agent and a hydrophilic polymer.

U.S. Pat. No. 8,486,448 describes a controlled release formulation comprising a core comprising a superabsorbent material, a controlled release coat surrounding the core; and a plurality of controlled release microparticles containing a pharmaceutically active agent.

U.S. Patent Application Publication 2011/0020451 describes a tamper-resistant thermoformed pharmaceutical dosage form having a breaking strength of at least 300 N and comprising an opioid, a physiologically acceptable acid and a polyalkylene oxide.

U.S. Patent Application Publication 2012/0148672 describes a coated modified release opioid-ion exchange resin complex comprising a pharmaceutically effective amount of an opioid bound to a pharmaceutically acceptable ion exchange resin complex; and a pH-independent, high tensile strength, water permeable, water insoluble, diffusion barrier coating.

In spite of the various tamper-resistant formulation approaches mentioned above, there is still a need for improved abuse deterrent formulations that better prevent common methods of dosage form tampering, and associated drug abuse administration routes without the incorporation of aversive agents and agonist/antagonists in the dosage form.

SUMMARY OF THE INVENTION

According to one embodiment, the present invention is related to a tamper-resistant dosage form that includes at least one therapeutic agent; at least one substrate; and at least one thermoplastic polymer, such that the at least one therapeutic agent and the at least one substrate form a therapeutic agent-substrate complex, the at least one thermoplastic polymer and optionally at least one pharmaceutical additive form a thermo-formable matrix, and the therapeutic agent-substrate complex is embedded in the thermo-formable matrix.

According to another embodiment, the present invention is related to a process of preparing a tamper-resistant dosage form, including the steps of: (1) blending at least one therapeutic agent and at least one substrate in a therapeutic agent-to-substrate ratio between 1:10 to 10:1; (2) reacting the at least one therapeutic agent and the at least one substrate to form a therapeutic agent-substrate complex; (3) forming a thermo-formable matrix blend with at least one thermoplastic polymer and optionally at least one pharmaceutical additive; (4) mixing the therapeutic agent-substrate complex and the thermo-formable matrix blend in a ratio between 1:20 to 20:1; (5) granulating the therapeutic agent-substrate complex and the thermo-formable matrix blend to form the tamper-resistant dosage form in which the therapeutic agent-substrate complex is embedded in the thermo-formable matrix; and (6) shaping the tamper-resistant dosage form into one of an immediate release or modified release tablet form and an immediate release or modified release multiparticulate form.

DETAILED DESCRIPTION OF THE INVENTION

An embodiment of the invention is a tamper-resistant dosage form that is resistant to various tampering modes. The tamper-resistant dosage form includes at least one drug, at least one substrate and at least one thermoplastic polymer and optionally at least one pharmaceutical additive that are arranged in the following manner: the at least one drug and the at least one substrate form a drug-substrate complex, the at least one thermoplastic polymer and optionally the at least one pharmaceutical additive form a thermo-formable matrix, and the drug-substrate complex is dispersed and embedded in the thermo-formable matrix.

It has been discovered that a therapeutic agent-substrate complex embedded into a thermo-formable matrix is effective against all forms of product tampering and drug abuse without the use of aversion agents and antagonists. It is critical that a complex of the therapeutic agent and a substrate is formed first prior to incorporation into the thermo-formable matrix in order for the formulation to provide tamper-resistance.

If only the therapeutic agent-substrate is used without the thermo-formable matrix as illustrated in Example 2; if the therapeutic agent is dispersed in the thermo-formable matrix without a substrate as illustrated in Example 3; or if only a blend of the therapeutic agent and the substrate but not a complex is dispersed in the thermo-formable matrix as illustrated in Example 4, then these formulations do not provide tamper-resistant formulations.

According to the invention, a "therapeutic agent" means a "drug" substance that elicits a pharmacologic response when administered by a patient or drug abuser. In the text, "therapeutic agent" and "drug" are used interchangeably. "Substrate" means a substance that interacts with the therapeutic agent to form a complex. Such a substrate could be a polyelectrolyte, an organic counter-ion, an inclusion compound, a pharmacologically inert organic component of a prodrug or an inorganic adsorbent. "Complex" means a chemical association of a drug substance with a substrate through ionic bonds, covalent bonds, polar covalent bonds, and hydrogen bonds.

According to the invention, the "thermo-formable matrix" comprises one or more thermoplastic polymers, and optionally one or more pharmaceutical additives that improve functionality and processability of the dosage forms. The thermo-formable matrix imparts plasticity and hardness to the dosage form. Embedding the drug-substrate complex in the thermo-formable matrix produces a synergistic effect that renders the dosage form more resistant to tampering. A "thermoplastic" polymer is a polymer that is solid at room temperature, and becomes pliable and moldable at elevated temperatures. A critical property of thermoplastic polymers is the glass transition temperature, a temperature where the polymer changes or transitions from a solid glassy phase into a rubbery phase. Glass transition temperatures are lowered by incorporating plasticizers.

According to the invention, "tampering" means an intentional or an unintentional manipulation of dosage forms in a manner that is not intended for by dosing instructions, such as chewing, crushing, breaking, grinding, extraction and volatilization.

Resistance to Chewing/Crushing/Breaking/Grinding

The dosage form in the invention does not break when a substantial force is applied. Milling or grinding the dosage form into fine powder using conventional methods, such as mortar and pestle or a hammer mill is impossible. Hardness measurement using standard hardness testers is not applicable. The dosage form according to the invention is, therefore, resistant to tampering by breaking, crushing, grinding and chewing.

Resistance to Extraction

Drug extraction from the dosage form according to the invention is eliminated or minimized through an integrated tamper-resistant mechanism. During the extraction process, the thermoplastic matrix generates a gel layer on the surface of the dosage form and limits liquid penetration into the core of the dosage form, which, in turn, limits the mobility of the therapeutic agent-substrate complex and hence the mobility of the therapeutic agent within the dosage form. The therapeutic agent-substrate complex present at the gel layer keeps the therapeutic agent tightly bound to the complex and does not make it available for extraction. Thus, the gel forming properties of the thermo-formable matrix and the embedded therapeutic agent-substrate complex provide a high degree of tamper resistance to extraction.

Resistance to Vaporization

Abusers often heat the dosage forms to vaporize the drug for smoking purposes. The dosage form according to the invention prevents vaporization by immobilizing the therapeutic agent within the therapeutic agent-substrate complex, and immobilizing the therapeutic agent-substrate complex within the theremo-formable matrix. The therapeutic agent-substrate complex has much lower vapor pressure than that of the free drug and as a result, requires much higher heat energy to liberate the free drug from the complex. In addition, the matrix prevents drug mobility and limits drug diffusion and vaporization through and out of the dosage form upon exposure to heat. Excessive heating of the dosage form with the intention of drug vaporization leads to decomposition and charring of formulation components which in turn may liberate obnoxious fumes that the abuser may not tolerate.

Therapeutic Agents

According to the invention, a "therapeutic agent" means a "drug" substance that elicits a pharmacologic response when administered by a patient or drug abuser. "Therapeutic agent" and "drug" are used interchangeably. Therapeutic agents covered by the present invention include those that are susceptible to abuse, i.e. "abuse-prone", and those that are not.

In one embodiment, the invention relates to an abuse-prone therapeutic agent that includes, but not limited to, narcotic opioids, CNS depressants, sedatives/hypnotics, stimulants, and decongestants.

Examples of narcotic opioids include, but not limited to, alfenatil, allylprodine, alphaprodine, anileridine, apomorphine, apocodeine, benzylmorphine, benzitramide, buprenorphine, butorphanol, clonitrazene, codeine, codeine methylbromide, codeine phosphate, codeine sulfate, cyclazocine, cyclorphen, cyprenorphine, desmorphine, dextromethorphan, dextromoramide, dezocine, diamromide, dihydrocodeine, dihydrocodeinone, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, hydrocodone, hydrocodone barbiturate, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, morphine derivatives, myrophine, nalbuphine, narceine, nicomorphine, norlevorphanol, normethadone, nalorphine, normorphine, norpipanol, ohmefentanyl, opium, oxycodone, oxymorphone, papaverum, pentazocine, phenadoxone, phenomorphan, phenazocine, phenoperidine, pheoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, naloxonazine, trindole, naltrindole isothiocyanate, naltriben, norbinaltorphimine, funaltrexmine, and salts or esters of any of the opioids, and mixtures thereof.

Examples of CNS depressants, sedatives or hypnotics include, but not limited to, acecabromal, bomisovalum, capruide, cabromal, ectylurea, chlorhexadol, ethcholorvynol, meparfynol, 4-methyl-5-thiazolethanol, tetrapentylalcohol, butoctamide, diethylbromoacetamide, ibrotamide, isovarleryl diethylamide, niaprazine, triacetamide, trimetozine, zolpidem, zopiclone; barbituric acid derivatives such as allobarbital, amobarbital, aprobarbital, barbital, brallabarbital, butabarbital sodium, butabarbital, butallylonal, buthetal, carbubarb, cyclobarbital, cyclopentobarbital, enallylpropymal, 5-ethyl-5-(1-piperidyl)barbituric acid, 5-furfuryl-5-isopropylbarbituric acid, heptabarbital, hexethal sodium, hexobarbital, mephobarbital, methitural, narcobarbital, nealbarbital, pentobarbital sodium, phenallylmal, phenobarbital, phenobarbital sodium, phenylmethylbarbituric acid, probarbital, propallylonal, proxibarbal, reposal, secobarbital sodium, thiopental, talbutal, tetrabarbital, thiobarbital, thiamylal, vinbarbital sodium, and vinylbital, benzodiazepine derivatives such as alprazolam, brotizolam, clorazepate, chlordiazepoxide, clonazepam, diazepam, doxefazepam, estazolam, flunitrazepam, flurazepam, haloxazolam, lorazepam, loprazolam, lormetazepam, nitrazepam, quazepam, temazepam, and triazolam; carbamates such as amylcarbamate, ethinamate, hexaprypymate, meparfynol carbamate, novonal and trichlorourethan; chloral derivatives such as carbocloral, chloral betaine, chloral formamide, chloral hydrate, chloralantipyrine, dichloralphenazone, pentaerithriol chloral and tricloflos; piperidinediones such as gluthemide, methylprylon, piperidione, taglutimide, thalidomide; quinazolone derivatives such as etaqualone, mecloquanone, and methaqualone; and others such as acetal, acetophenone, aldol, ammonium valerate, amphenidone, d-bornyl-a-bromoisovalerate, d-bornylisovalerate, calcium 2-ethylbutanoate, carfinate, a-chlorolose, clomethiazole, cypripedium, doxylamine, etodroxizine, etomidate, fenadiazole, homofenazine, hydrobromic acid, mecloxamine, methyl valerate, opium, paraldehyde, perlapine, propiomazine, rimazafone, sodium oxybate, sulfomethylmethane and sulfonmethane, and mixtures thereof.

Examples of stimulants include, but not limited to, amphethamine, dextroamphethamine, levoamphetamine, methamphetamine, methylphenidate, phenmetrazine, modatinil, avafinil, armodafinil, and ampalimes; cannabinoids such as tetrahydro-cannabinol, nabilone; ketamine, tiletamine, dextromethorphan, ibogaine, dixocilpine; anabolic steroids such as androisoxazole, androstenediol, bolandiiol, clostebol, ethylesternol, formyldienolone, 4-hydroxy-19-nortestosterone, methandriol, methenolone, methyltrienolone, nandrolone, nandrolone deconate, nandrolone p-hexyloxyphenylpropionate, nandrolone phenpropionate, norbolethone, oxymestrone, pizotyline, quinbolone, stenbolone and trenbolone; anorexics such as a minorex, amphecloral, benzaphetamine, chlorphentermine, clobenzorex, cloforex, clortermine, cyclexedrine, diethylpropion, diphemethoxidine, n-ethylamphetamine, fenbutrazate, fenfluramine, fenproporex, furfurylmethylamphetamine, levophacetoperate, mazindol, mefenorex, metamfeproamone, norpseudoephedrine, phendimetrazine, phendimetrazine trtrate, phentermine, phenylpropanolamine hydrochloride and picilorex and mixtures thereof.

Examples of decongestants include, but not limited to, pseudoephedrine, ephedrine, levo-methamphetamine, phenylpropanolamine, propylhexedrine and synephrine, and mixtures thereof.

In another embodiment, the invention relates to a therapeutic agent that is not susceptible to abuse, such as, but not limited to, atenolol, albendazole, alendronate, alprostadil, allopurinol, amlexanox, anagrelide, aminophylline, alitretinoin, amodiaquine, astemizole, atovaquone, aztreonam, atorvastatin, azlocillin, baclofen, benazepril, benzonatate, bitolterol mesylate, brompheniramine, cabergoline, carisoprodol, celecoxib, cefpiramide, chlorothiazide, chlormezanone, cimetidine, cetirizine, cefotaxime, ciprofloxacin, cephalexin, chloroquine, clomocycline, cyclobenzaprine, cyproheptadine, cyproheptadine, cefmenoxime, cyclophosphamide, ciclopirox, cladribine, chlorpheniramine, chlorzoxazone, clemastine, clofarabine, cytarabine, dacarbazine, dantrolene, daunorubicin, dexamethasone, diclofenac, diethylcarbamazine, diphenhydramine, diphenylpyraline, disopyramide, diltiazem, dopamine, dofetilide, doxazosin, enoxacin, epirubicin, eplerenone, erlotinib, ertapenem, etoposide, exemestane, ezetimibe, fexofenadine, flucloxacillin, fulvestrant, fenofibrate, fenoprofen, fenoldopam, fluocinonide, flunisolide, fluorouracil, gefitinib, gemcitabine, grepafloxacin, guaifenesin, halofantrine, ibuprofen, ibandronate, ipratropium, irinotecan, isosorbide mononitrate, ipratropium, ivermectin, ketoconazole, ketoprofen, ketorolac, levamisole, letrozole, levosimendan, levofloxacin, lovastatin, loratadine, lymecycline, loracarbef, lisuride, meclofenamate, mefloquine, meloxicam, methocarbamol, methylbromide, metolazone, methyldopa, methdilazine, mequitazine, mitotane, mivacurium, moxifloxacin, mometasone, midodrine, milrinone, nabumetone, naproxen, nifedipine, nilutamide, nedocromil, omeprazole, olmesartan, oxaliplatin, oxamniquine; orphenadrine, pantoprazole, pefloxacin, pentamidine, penicillamine, pemetrexed, perhexyline, phenylbutazone, pipobroman, piroxicam, propranolol, phentermine, phentolamine, piperacillin, piperazine, primaquine, piroxicam, pivoxil, praziquantel, probenecid, porfimer, propafenone, prednisolone, proguanil, pyrimethamine, quinine, quinidine, ranolazine, remikiren, rofecoxib, salmeterol, sulfanilamide, sulfadiazine, suprofen, sulfinpyrazone, tenoxicam, triamterene, tolmetin, toremifene, tolazoline, tamoxifen, teniposide, theophylline, terbutaline, terfenadine, thioguanine, tolmetin, trimetrexate, triprolidine, trovafloxacin, verapamil, valsartan, vinorelbine, valrubicin, vincristine, valdecoxib and mixtures thereof.

Thermoplastic Polymers

The invention relates to a tamper-resistant dosage form that comprises one or more thermoplastic polymers such as, but not limited to, cellulose derivatives, vinyl derivatives, acrylates, polyoxides, polysaccharides and polyglycols. A "thermoplastic" polymer is a polymer that is solid at room temperature, and becomes pliable and moldable at elevated temperatures. A critical property of thermoplastic polymers is the glass transition temperature, a temperature where the polymer changes or transitions from a solid glassy phase into a rubbery phase. Glass transition temperatures are lowered by incorporating plasticizers.

Examples of thermoplastic polymers suitable for the present invention include, but not limited to, hydroxypropyl cellulose, hydroxylpropyl methyl cellulose, methyl cellulose, methylmethacrylate, carrageenan, xanthan gum, polyethylene glycol, polyethylene oxide, polypropylene glycol, polyvinyl acetate, polyvinyl alcohol, polyvinyl pyrrolidone, butyl/methylmethacrylate-dimethylaminoethylmethacrylate copolymer, polyvinyl caprolactam-polyvinyl acetate-polyethylene glycol, and hydroxylethyl cellulose, and mixtures thereof.

Substrates

The invention relates to a tamper-resistant dosage form comprising one or more substrates such as polyelectrolytes, inorganic adsorbents, organic acids, inclusion compounds, fatty acids and pharmacologically inert components of prodrugs. According to the invention, a "substrate" is a substance that interacts with a therapeutic agent to form a complex. "Complex" means a chemical association between a therapeutic agent and a substrate through ionic bonds, covalent bonds, polar covalent bonds, and hydrogen bonds.

In one aspect, substrates comprise polyelectrolytes consisting of natural polyelectrolytes selected, for example, from the group consisting of nucleic acids, poly(L-lysine), poly(L-glutamic acid), carrageenan, alginates, and hyaluronic acid, and mixtures thereof; chemically modified polyelectrolyte selected, for example, from the group consisting of pectin, chitosan (deacetylation of chitin), cellulose-based, starch-based and dextran-based polymers and mixtures thereof; and synthetic polyelectrolytes selected from, for example, poly(vinylbenzyl trialkyl ammonium), poly(4-vinyl-N-alkyl-pyridimiun), poly(acryloyl-oxyalkyl-trialkyl ammonium), poly(acryamido-alkyl-trialkyl ammonium), poly(diallydimethyl-ammonium), poly(acrylic or methacrylic acid), and poly(itaconic acid) and maleic acid/diallyamine copolymer, crosslinked copolymers such as carbopols, crosscarmellose, ion exchange resins and mixtures thereof.

Examples of ion exchange resins include sulfonated copolymer of styrene and divinylbenzene, a carboxylate copolymer of styrene and divinylbenzene, a copolymer of styrene and divinylbenzene containing quaternary ammonium groups such as Amberlite® IR-120(sodium salt of styrene divinylbenzene sulfonate copolymer), Amberlite® XE-69 (sodium salt of styrene divinylbenzene sulfonate copolymer), Amberlite® IRP-64 (methacrylic acid divinylbenzene carboxylate copolymer), Amberlite® IRP-69 (sodium salt of styrene divinylbenzene sulfonate copolymer), Dowex® 50WX2 (sulfonate of styrene and divinylbenzene copolymer consisting of 2% cross linking), Dowex® 50WX4 (sulfonate of styrene and divinylbenzene copolymer consisting of 4% cross linking), Dowex® 50WX8 (sulfonate of styrene and divinylbenzene copolymer consisting of 8% cross linking), Duolite® AP 143 (styrene and divinylbenzene with quaternary ammonium functional group), Indion® 204 (crosslinked polyacrylic polymer with carboxylic acid functional group having particle size 45% larger than 75 micron), Indion® 214 (crosslinked polyacrylic polymer with carboxylic acid functional group having particle size 45% larger than 75 micron), Indion® 234 (potassium salt of crosslinked polyacrylic polymer having particle size 70% larger than 75 microns), Indion® 264 (crosslinked polyacrylic polymer with carboxylic acid functional group having particle size 30% larger than 75 microns), Tulsion® 335 (crosslinked polyacrylic polymer with carboxylic acid functional group), Tulsion® 339 (potassium salt of crosslinked polyacrylic polymer with carboxylic acid functional group), and Tulsion® 343 (crosslinked polyacrylic polymer with carboxylic acid functional group) and mixtures thereof.

In another aspect, substrates comprise inorganic adsorbents selected, for example, from the group consisting of but not limited to aluminum silicate, attapulgite, bentonite, calcium silicate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, zeolite, and zirconium silicate and mixtures thereof.

In yet another aspect, substrates comprise inclusion compounds selected, for example, from the group consisting of but not limited to α-cyclodextrins, β-cyclodextrins and γ-cyclodextrins.

In yet another aspect, substrates comprise organic acids selected, for example, from the group consisting of but not limited to acetates, besylates, tartrates, citrates, maleates, succinates, fumarates, adipiates, and oxalates and mixtures thereof.

In yet another aspect, substrates comprise fatty acids selected from the group, for example, consisting of but not limited to arachidonic acid, capric acid, caprylic acid, dihomo-γ-linoleic acid, docesenoic acid, docosatetraenoic acid, docosohexaconic acid, docosopentanoic acid, eicosapentanoic acid, gondoic acid, lauric acid, linoleic acid, α-linoleic acid, 6-linoleic acid, myristic acid, nervonic acid, oleic acid, oleostearic acid, palmitic acid, palmitoleic acid, stearic acid, and vaccenic acid and mixtures thereof.

In yet another aspect, substrates comprise pharmacologically-inert organic component of prodrugs is selected, for example, from the group consisting of but not limited to amides and esters.

Pharmaceutical Additives

The invention relates to a dosage form optionally comprising pharmaceutical additives that improve functionality and processability of dosage forms. Pharmaceutical additives that are incorporated in formulations consist of plasticizers, waxes, surfactants, inorganic fillers, anti-adherents, erosion enhancers, anti-oxidants, and buffering agents.

Examples of plasticizers include, but not limited to, dibutyl sebacate, glycerol, polyethylene glycol, propylene glycol, triacetin, tributyl citrate, and triethyl citrate and mixtures thereof.

Examples of waxes include, but not limited to, bees wax, candilila wax, carnuba wax, and paraffin wax and mixtures thereof.

Examples of surfactants include, but not limited to, alkyl benzene sulfones, alkyl sulfates, ether carboxylates, glycerol/propylene glycol fatty acid esters, hexadecyl triammonium bromide, hydroxylated lecithin, lauryl carnitine, lower alcohol-fatty acid esters, mono-/di-glycerides, Ovothin®

(phospholipid extracted from egg), polyethylene glycol alkyl ethers, polyethylene glycol-fatty acid monoesters, polyethylene glycol-fatty acid diesters, polyethylene glycol-glycerol esters, polyethylene glycol phenols, polyethylene glycol-sorbitan fatty acid esters, polyglyceride fatty acids, polyoxyethylene-polyoxypropylene block copolymers, propylene glycol-fatty acid esters, sodium cholate, sodium lauryl sulfate, sodium palmitate, sodium taurocholate, sorbitan-fatty acid esters, sterol and sterol derivatives, sugar esters, transesterification products of oils and alcohols and mixtures thereof.

Examples of inorganic fillers include, but not limited to silicon dioxide, aluminum silicate, attapulgite, bentonite, calcium silicate, calcium carbonate, dicalcium phosphate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, talc, titanium dioxide, zeolite, and zirconium silicate, and mixtures thereof.

Examples of anti-adherents include, but not limited to, calcium carbonate, dicalcium phosphate, kaolin, talc, and titanium dioxide, and mixtures thereof.

Examples of erosion enhancers include, but not limited to, low molecular weight water soluble polymers such as hydroxyethyl cellulose, hydroxypropyl methyl cellulose, and polyvinyl pyrrolidone; polyols, such as mannitol, malitol, sorbitol, and xylytol, and surface active agents such as sodium lauryl sulfate, and Polysorbate 80, and mixtures thereof.

Examples of antioxidants include, but not limited to, butylhydroxytoulene, butylhydroxyanisole, propyl gallate, ascorbic acid and vitamin E-TPGS, and mixtures thereof.

Examples of buffering agents include, but not limited to, phosphates, citrates, acetates, oxides and carbonates, and mixtures thereof.

Tamper-Resistant Dosage Forms

In one embodiment, the invention relates to monolithic and multiparticulate dosage form comprising a therapeutic agent-substrate complex, one or more thermoplastic polymers, and one or more pharmaceutical additives.

Preparation of Tamper-Resistant Dosage Form

The tamper-resistant dosage form of the present invention can be prepared according to the steps of:

(1) Blending at least one therapeutic agent and at least one substrate in a drug-to-substrate ratio between 1:10 to 10:1;

(2) Reacting the at least one therapeutic agent and the at least one substrate to form a therapeutic agent-substrate complex;

(3) Forming a thermo-formable matrix blend with at least one thermoplastic polymer and optionally a pharmaceutical additive;

(4) Mixing the therapeutic agent-substrate complex and the thermo-formable matrix blend in a ratio between 1:20 to 20:1;

(5) Granulating the therapeutic agent-substrate complex and the thermo-formable matrix blend to form the tamper-resistant dosage form in which the therapeutic agent-substrate complex is embedded in the thermo-formable matrix; and (6) Shaping the tamper-resistant dosage form into one of tablet form and multiparticulate form.

Furthermore, the reacting step of (2) can be carried out by a reactive extrusion process. The granulating step of (5) can be carried out by a hot melt extrusion process, or optionally by a wet granulation or a dry granulation process.

A. Preparation of Therapeutic Agent-Substrate Complex:

The therapeutic agent-substrate complex is prepared using a novel reactive extrusion process. The reactive extrusion process is fast and continuous compared to other commonly used processes. It allows the complexation process to proceed at a faster rate by providing flexibility in reaction temperatures and online incorporation of pH modifiers and other additives that promote complex formation. The extruder, which behaves as a reactor, is preferably a twin screw extruder. It comprises uniquely assembled conveying and mixing elements and temperature controlled modular barrels that constitute a continuous reaction vessel. Along the extruder length, one or more liquid injection and powder feed ports are inserted in the barrels, wherein the number and location of the ports are dictated by the complexation process requirements. Alternatively, the complex may be prepared by a variety of processes known in the art. The drug to substrate ratio in the complex varies from 1:10 to 10:1, preferably from 1:5 to 5:1, and more preferably from 1:3 to 3:1.

B. Embedding Therapeutic Agent-Substrate Complex within Thermo-Formable Matrix

The therapeutic agent-substrate complex is blended with the thermoplastic polymer and optionally at least one pharmaceutical additive, and the blend melt granulated at processing temperatures of less than 200° C. and preferably less than 150° C. using a twin-screw extruder. Alternatively, a blend of the thermoplastic polymer and optionally at least one pharmaceutical additive is fed into the extruder through the first powder feed port and allowed to melt before the therapeutic agent-substrate complex is introduced through a second powder feed port downstream from the first feed port and mixed with the molten mass in the extruder. In both procedures, the melt granulated material or extrudate is shaped downstream to provide tamper-resistant tablets or multiparticulates that are filled into capsules or compressed into tablets. The ratio of the therapeutic agent-substrate complex to the thermo-formable matrix varies from 1:20 to 20:1, and preferably from 1:10 to 10:1, and more preferably from 1:5: to 5:1.

Resistance to Tampering

In one embodiment, the tamper-resistant dosage form according to the invention is resistant to breaking, chewing, crushing and grinding. The therapeutic agent-substrate complex is embedded into a thermo-formable matrix to form a dosage form that does not break or deform at least for up to 350 N when tested on a tablet hardness tester. Storing the dosage form at 0° C. temperature prior to the application of force does not bring about a change in the physical properties of the dosage form. Communion of the dosage form using conventional milling equipment is not possible.

Examples of prescription drugs abused by swallowing include; barbiturates such as phenobarbital and secobarbital; opioids such as morphine, codeine, fentanyl, methadone, oxycodone HCl, hydrocodone bitartrate, hydromorphone, oxymorphone, meperidine, propoxyphene and dextromethorphan; benzodiazepines such as diazepam and clonazepam; sleep medications such as zolpidem and zaleplon; and stimulants such as amphetamine and methylphenidate.

In another embodiment, the dosage form according to the invention is resistant to snorting. Since the dosage form does not get reduced into fine powder, it does not allow the abuser to administer the therapeutic agent intra-nasally to facilitate drug absorption through the lining of the nasal passages by snorting. Even if the tablet were to be pulverized, the therapeutic agent would still be tightly bound to the substrate and not become available for intra-nasal absorption. Examples of prescription drugs abused by snorting include:

opioids such as morphine, codeine, fentanyl, methadone, oxycodone HCl, hydrocodone bitartrate, hydromorphone, oxymorphone, meperidine and propoxyphene; sleep medications such as zolpidem and zaleplon; stimulants such as amphetamine and methylphenidate.

In yet another embodiment, the dosage form according to the invention prevents extraction of the therapeutic agent using commonly used organic and household solvents. Continuous agitation of the dosage form or its fragments in 30 mL or 200 mL extraction volume for at least 8 hours leads to insignificant drug release. As a result, the dosage form is expected to be resistant to abuse by injection. Examples of prescription drugs abused by injection include: barbiturates, such as phenobarbital and secobarbital; opioids such as morphine, codeine, fentanyl, methadone, oxycodone HCl, hydrocodone bitartrate, hydromorphone, oxymorphone, meperidine and propoxyphene; stimulants such as amphetamine and methylphenidate.

In yet another embodiment, the present invention relates to a dosage form that prevents drug abuse by smoking where the therapeutic agent needs to vaporize for inhalation after exposure of the dosage form to heat. For example, the dosage form is placed on top of an aluminum foil, and heated from underneath the foil to vaporize the therapeutic agent. The therapeutic agent-substrate complex has much lower vapor pressure than that of the free drug, which would require much higher heat energy to liberate the free drug from the complex. The matrix also provides additional barrier to drug vaporization. Excessive heating of the dosage form leads to decomposition and charring of formulation components. Examples of prescription drugs abused by smoking include: fentanyl and its analogs, amphetamines, and morphine.

In yet another embodiment, the present invention relates to two or more dosage forms that provide similar abuse deterrent properties, and yet generate a variety of dissolution profiles that meet predetermined pharmacokinetic requirements. For example, multi-solvent extraction data from dosage forms comprising five different formulations demonstrated similar but insignificant drug release irrespective of the agitation time and extraction volume. The same dosage forms, however, exhibited release data that vary from over 90% in 4 hours to greater than 90% in 24 hours. Substituting one therapeutic agent for another in a given formulation according to the invention does not alter the abuse deterrent potential and dissolution profiles of the dosage form.

In yet another embodiment, the present invention relates to a dosage form that minimizes or eliminates oxidative or hydrolytic decomposition of therapeutic agents. Many therapeutic agents, including opioids, undergo oxidative or hydrolytic degradation when exposed to acidic or alkaline aqueous environments or thermal stresses, or both. Moreover, some pharmaceutical additives, such as polyethylene oxide, contain trace amounts of peroxides and promote oxidation of the therapeutic agent upon storage or during thermal processing, and, as a result, anti-oxidants and buffering agents are routinely added to formulations to prevent potential for degradation of therapeutic agents through the shelf-life of the dosage forms. In the present invention, the formation and incorporation of the drug-substrate complex within the thermo-formable matrix obviates the need for incorporating anti-oxidants and buffering agents in the dosage form.

In yet another embodiment, the invention relates a tamper-resistant dosage form comprising tablets and multiparticulates that release the therapeutic agent for up to 24 hours. Multiparticulates are blended with other tableting excipients and compressed prior to dissolution testing. During dissolution, the compressed tablets disintegrate in less than a minute to regenerate the original maltiparticulates.

In another aspect, the tamper-resistant dosage form is prepared by blending the therapeutic agent-substrate complex, a thermoplastic polymer and at least one pharmaceutical additive, and granulated using conventional dry granulation or wet granulation/drying processes followed by compression into tablets. Once again the therapeutic agent-substrate complex is embedded within the thermo-formable matrix in the dosage form.

EXAMPLES

The following examples are included to demonstrate certain embodiments of the present invention and not intended to be limiting. They are for illustrative purposes only and it is to be noted that changes and variations can be made without departing from the spirit and scope of the invention.

Example 1

Preparation of Drug-Substrate Complex

A general preparation of a drug-substrate complex is described in this example. For example, a drug-ion exchange resin complex can be prepared from a blend of the drug and Amberlite IRP 69 using a novel reactive extrusion process. A 16 mm twin-screw extruder was used as a reactor, although larger size extruders could be used if the desired yield is high. The drug and Amberlite IRP 69 were pre-blended and the blend introduced into the extruder through a powder feed port. At a second port downstream from the first feed port, deionized water was added at a controlled rate to generate a heavy suspension. The extrusion process was carried out at a screw speed of 300 rpm and processing temperatures of 25° C. Alternatively, the drug-Amberlite IRP complex can be prepared by other methods known in the art.

The suspension was collected and washed using deionized water to remove any free uncomplexed drug. The supernatant was decanted and discarded. The residue comprising a drug-ion exchange resin complex was then dried in an air forced oven at 40° C.

Drug loading was determined using the following procedure: 20 mg of the drug ion-exchange complex was added to 200 mL of 2% NaCl solution in a flask and then agitated for 4 hrs. The suspension was filtered and the residue discarded. The amount of free drug in the supernatant was then determined.

Example 2

Propranolol Ion-Exchange Resin Complex Particles

In this example, a therapeutic agent (propranolol), and a substrate (ion-exchange resin) were used to form a complex. No thermoplastic polymer, and thus no thermoformable matrix were included in this formulation. Propranolol ion exchange resin complex particles were prepared using the procedure described in Example 1.
Dissolution Studies:

Dissolution studies on propranolol ion exchange resin complex particles were conducted in 900 mL of pH 6.8 Phosphate buffer (0.05M) consisting of 0.2% sodium chloride using USP Apparatus II (Paddle) at 75 rpm. The dissolution data is given below:

| Time (h) | % Released |
|---|---|
| 0.25 | 78 |
| 0.5 | 89 |
| 1 | 96 |
| 2 | 98 |

Extraction Studies

Extraction studies were conducted on propranolol ion exchange resin complex in different solvents using a wrist action shaker at a speed of 416 rpm and 18° angle. Samples were withdrawn at 15 minutes and 60 minutes and the drug release was determined using a spectrophotometer. The results are given below:

| Extraction Solvent | % Released | |
|---|---|---|
| | 15 min | 60 min |
| 0.9% NaCl solution | 3.4 | 3.6 |
| Methanol | 0.4 | 0.5 |
| Water | 0.5 | 0.4 |
| 0.1N HCl | 1.4 | 1.4 |
| Ethanol 40% | 0.4 | 0.4 |
| 0.1N NaOH | 2.7 | 2.5 |
| Ethanol 96% | 0.2 | 0.2 |
| Isopropanol | 0.6 | 0.8 |
| Ethylacetate | 0.2 | 0.2 |

The dissolution studies showed that the propranolol ion exchange complex in the absence of a thermoformable matrix did not demonstrate extended release properties, releasing almost 100% of the drug within 2 hrs. On the other hand, extraction studies showed that the complex released very low amount of drug in all extraction solvents. The formulation without a thermoplastic polymer provided good tamper resistance property with regard to extraction, but failed to generate the desired extended release characteristics.

Example 3

Propranolol HCl Multiparticulates

In this example, a therapeutic agent (propranolol), thermoplastic polymers (hydroxypropylcellulose I and II) and an additive (silicon dioxide) were used. No substrate, and thus no therapeutic agent-substrate complex were included in this formulation.

Propranolol HCl (free drug), hydroxypropylcellulose (I), hydroxypropylcellulose (II) and silicon dioxide were blended, fed into a 16 mm twin screw extruder and extruded. The extrusion process was carried out at a processing temperature of 140° C. and a screw speed of 200 rpm. The extrudates were shaped into multiparticulates downstream. A portion of the multiparticulates were mixed with external excipients and compressed into tablets. The tablets and multiparticulates were collected and stored in high density polyethylene (HDPE) bottles.

| Ingredient | % w/w |
|---|---|
| Propranolol HCl | 25 |
| Hydroxypropyl cellulose (I) (M.W. 370,000) | 35.5 |
| Hydroxypropyl cellulose (II) (M.W. 80,000) | 35.5 |
| Silicon dioxide | 4 |
| Total | 100 |

Dissolution Studies:

Dissolution studies were conducted on the tablets in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
|---|---|
| 0.25 | 41 |
| 0.5 | 69 |
| 1 | 100 |

Extraction Studies

Extraction studies were conducted on the multiparticulates in different solvents using a wrist action shaker at a speed of 416 rpm and 18° angle. Samples were withdrawn at 15 minutes and 60 minutes and the drug release determined using a spectrophotometer. The results are given below:

| Extraction Solvent | % Released | |
|---|---|---|
| | 15 min | 60 min |
| 0.9% NaCl solution | 62.6 | 94.2 |
| Methanol | 94.7 | 99.3 |
| Water | 77.4 | 94.2 |
| 0.1N HCl | 68.7 | 90.8 |
| Ethanol 40% | 42.4 | 85.9 |
| 0.1N NaOH | 4.3 | 5.0 |
| Ethanol 96% | 42.8 | 80.7 |
| Isopropanol | 22.5 | 44.1 |
| Ethylacetate | 23.4 | 25.4 |

Dissolution studies indicated that multiparticulates comprising of propranolol HCl, but without a substrate, dispersed in thermo-formable matrix lead to 100% drug release within 1 hr. Extraction studies also showed that the multiparticulates release significant levels of drug in almost all extraction solvents. The formulation without a substrate thus exhibited neither acceptable tamper resistance nor sufficient extended release properties.

Example 4

Propranolol HCl and Ion-Exchange Resin Blend-Based Multiparticulates

In this example, a therapeutic agent (propranolol), a substrate (Amberlite IRP 69), thermoplastic polymers (hydroxypropylcellulose I and II) and an additive (silicon dioxide) were used. The therapeutic agent and the substrate were only blended without the formation of a complex.

Propranolol HCl (free drug), Amberlite IRP 69 (uncomplexed resin), hydroxypropylcellulose (I), hydroxypropylcellulose (II) and silicon dioxide were blended, fed into a 16 mm twin screw extruder and extruded. The extrusion process was carried out at processing temperatures of 140° C. and a screw speed of 200 rpm. The extrudates were shaped into multiparticulates downstream. A portion of the multiparticulates were mixed with external excipients and compressed into tablets. The tablets and multiparticulates were collected and stored in high density polyethylene (HDPE) bottles.

| Ingredient | % w/w |
| --- | --- |
| Propranolol HCl | 25 |
| Amberlite IRP 69 (Ion-exchange resin) | 25 |
| Hydroxypropyl cellulose (I) (M.W. 370,000) | 23 |
| Hydroxypropyl cellulose (II) (M.W. 80,000) | 23 |
| Silicon dioxide | 4 |
| Total | 100 |

Dissolution Studies:

Dissolution studies were conducted on the tablets in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
| --- | --- |
| 0.25 | 43 |
| 0.5 | 63 |
| 1 | 93 |
| 2 | 100 |

Extraction Studies

Extraction studies were conducted on the multiparticulates in different solvents using a wrist action shaker at a speed of 416 rpm and 18° angle. Samples were withdrawn at 15 minutes and 60 minutes and the drug release was determined using a spectrophotometer. The results are given below:

| Extraction Solvent | % Released | |
| --- | --- | --- |
| | 15 min | 60 min |
| 0.9% NaCl solution | 45.6 | 58.3 |
| Methanol | 75.4 | 77.6 |
| Water | 54.5 | 57.2 |
| 0.1N HCl | 41.2 | 40.6 |
| Ethanol 40% | 44.6 | 45.1 |
| 0.1N NaOH | 5.7 | 5.4 |
| Ethanol 96% | 64.8 | 69.5 |
| Isopropanol | 36.4 | 55.2 |
| Ethylacetate | 9.3 | 12.3 |

Dissolution studies indicated that multiparticulates comprising of propranolol HCl and ion-exchange resin physical blend (uncomplexed) dispersed in thermo-formable matrix lead to 100% drug release within 2 hr. Extraction studies also showed that the multiparticulates release significant levels of drug in almost all extraction solvents. The formulation that did not use a drug-substrate complex thus exhibited neither acceptable tamper resistance nor sufficient extended release properties.

Example 5

Propranolol Ion-Exchange Multiparticulates

The propranolol ion exchange complex, hydroxypropylcellulose (I), hydroxypropylcellulose (II) and silicon dioxide were blended, fed into a 16 mm twin screw extruder and extruded. The extrusion process was carried out at a processing temperature of 140° C. and a screw speed of 200 rpm. The extrudates were shaped into multiparticulates downstream. A portion of the multiparticulates were mixed with external excipients and compressed into tablets. The tablets and multiparticulates were collected and stored in high density polyethylene (HDPE) bottles.

| Ingredient | % w/w |
| --- | --- |
| Propranolol Ion Exchange Resin Complex | 50 |
| Hydroxypropyl cellulose (I) (M.W. 370,000) | 23 |
| Hydroxypropyl cellulose (II) (M.W. 80,000) | 23 |
| Silicon dioxide | 4 |
| Total | 100 |

Dissolution Studies:

Dissolution studies were conducted on the tablets in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
| --- | --- |
| 0.25 | 0.5 |
| 0.5 | 4 |
| 1 | 13 |
| 2 | 35 |
| 3 | 62 |
| 4 | 77 |

Extraction Studies

Extraction studies were conducted on the multiparticulates in different solvents using a wrist action shaker at a speed of 416 rpm and 18° angle. Samples were withdrawn at 15 minutes and 60 minutes and the drug release was determined using a spectrophotometer. The results are given below:

| Extraction Solvent | % Released | |
| --- | --- | --- |
| | 15 min | 60 min |
| 0.9% NaCl solution | 3.1 | 4.5 |
| Methanol | 2.3 | 2.6 |
| Water | 0.9 | 3.4 |
| 0.1N HCl | 1.5 | 2.1 |
| Ethanol 40% | 1.0 | 1.1 |
| 0.1N NaOH | 5.5 | 5.7 |
| Ethanol 96% | 1.9 | 5.0 |
| Isopropanol | 1.0 | 2.5 |
| Ethylacetate | 0.7 | 1.2 |

Dissolution studies indicated that tablets comprising multiparticulates consisting of propranolol ion-exchange resin complex embedded in a thermo-formable matrix exhibited extended release profile in contrast to the free drug in a matrix. About 77% was released after 4 hours. Extraction studies showed that the multiparticulates released an insignificant amount of drug in all extraction solvents. Incorporation of the drug substrate complex into a thermo-formable matrix provided excellent tamper resistance and extended release profile, a functional performance that could not be achieved by either of them when employed separately.

Example 6

Dextromethorphan-Ion Exchange Multiparticulates

Dextromethorphan ion exchange resin complex was prepared using the procedure described in Example 1.

Two different formulations (F-1 and F-2) containing dextromethorphan-Ion exchange resin complex were blended, fed into a 16 mm twin screw extruder and extruded at processing temperatures of 140° C. and screw speed of 200 rpm. The extrudate was converted into multiparticulates downstream. The multiparticulates were blended with appropriate external excipients to generate a tablet blend and subsequently were compressed into tablets. The tablets were collected and stored in high density polyethylene (HDPE) bottles.

| Ingredient | F-1 | F-2 |
|---|---|---|
| | % w/w | |
| Dextromethorphan Ion Exchange Resin Complex | 50 | 50 |
| Hydroxypropyl cellulose (I) (M.W. 370,000) | — | 36.75 |
| Hydroxypropylcellulose (II) (M.W. 80,000) | — | 12.25 |
| Hydroxypropyl cellulose (III) (M.W. 1,150,000) | 40 | — |
| Polyethylene glycol (M.W. 400) | 4.5 | — |
| Talc | 4.5 | — |
| Silicon dioxide | 1.0 | 1.0 |
| Total | 100 | 100 |

Dissolution Studies:

Dissolution studies were conducted on the tablets in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released | |
|---|---|---|
| | F-1 | F-2 |
| 1 | 21 | 41 |
| 2 | 36 | 82 |
| 3 | 48 | 100 |
| 4 | 61 | |
| 5 | 66 | |
| 6 | 69 | |
| 7 | 71 | |
| 8 | 72 | |

Extraction Studies

Extraction studies were conducted on the multiparticulates in different solvents using a wrist action shaker at a speed of 416 rpm and 18° angle. Samples were withdrawn at 15 minutes and 60 minutes and drug release was determined using a UV-spectrophotometer. The results are given below:

| Extraction Solvent | % Released | | | |
|---|---|---|---|---|
| | F-1 | | F-2 | |
| | 15 min | 60 min | 15 min | 60 min |
| Methanol | 2.1 | 2.8 | 1.1 | 5.5 |
| Water | 0.2 | 0.5 | 1.8 | 3.4 |
| 0.1N HCl | 2.4 | 3.9 | 5.0 | 7.3 |
| Ethanol 40% | 0.8 | 1.6 | 1.7 | 3.5 |
| 0.1N NaOH | 2.4 | 4.3 | 1.7 | 2.9 |
| Ethanol 96% | 1.2 | 2.4 | 2.5 | 4.9 |
| Isopropanol | 0.7 | 1.2 | 1.5 | 3.1 |
| Ethylacetate | 0.7 | 1.1 | 1.3 | 2.0 |

Ideally, a dosage form should provide an in vitro release profile that achieves a target therapeutic effect and at the same time maintain the tamper resistant property to dissuade drug abusers. The data indicates that the invention satisfies the requirement: different dextromethorphan multiparticulate formulations can provide different dissolution profiles and yet have similar tamper resistant properties as demonstrated by the low level of extractability using different extraction solvents.

Example 7

Dextromethorphan-Ion Exchange Tablets

A mixture of Dextromethorphan ion exchange resin complex, hydroxypropylcellulose (I), hydroxypropylcellulose (II) and polyethylene glycol were blended and fed into a 16 mm twin screw extruder and extruded at extrusion temperatures of 100° C. and a screw speed of 200 rpm. The extrudate was shaped into tablets downstream. The tablets were collected and stored in high density polyethylene (HDPE) bottles.

| Ingredient | % w/w |
|---|---|
| Dextromethorphan Ion Exchange Resin Complex | 50 |
| Hydroxypropyl cellulose (I) (M.W. 370,000) | 26.25 |
| Hydroxypropylcellulose (II) (M.W. 80,000) | 8.75 |
| Polyethylene glycol (M.W. 400) | 15 |
| Total | 100 |

Dissolution Studies:

Dissolution studies were conducted on the tablets in pH 6.8 Phosphate buffer (0.05M) consisting of 0.2% sodium chloride using USP Apparatus I (basket) at 100 rpm. The dissolution data is given below:

| Time (h) | % Released |
|---|---|
| 1 | 7 |
| 2 | 15 |
| 3 | 21 |
| 4 | 28 |
| 5 | 34 |
| 6 | 40 |
| 7 | 45 |
| 8 | 49 |

Extraction Studies

Extraction studies were conducted on the tablets in different solvents using a wrist action shaker at a speed of 416 rpm and 18° angle. Samples were withdrawn at 15 minutes and 60 minutes, and the drug release was determined using a UV-spectrophotometer. The results are given below:

| | Intact Tablets | |
|---|---|---|
| Extraction | % Released | |
| Solvent | 15 min | 60 min |
| Methanol | 1.2 | 2.3 |
| Water | 0.2 | 0.3 |
| 0.1N HCl | 1.7 | 2.7 |
| Ethanol 40% | 0.5 | 0.7 |
| 0.1N NaOH | 6.9 | 6.2 |
| Ethanol 96% | 0.7 | 1.5 |
| Isopropanol | 0.3 | 0.6 |
| Ethylacetate | 0.3 | 0.7 |

The data indicates that the invention permits the preparation of dextromethorphan tablets that have extended release dissolution profiles and at the same time provide tamper resistance as demonstrated by the low level of extractability of the therapeutic agent from the tablets using different extraction solvents.

Example 8

Propranolol-Ion Exchange Tablets

Two different formulations (F-3 and F-4) containing Propranolol-Ion exchange resin complex were blended and fed into a 16 mm twin screw extruder and extruded at processing temperatures of 100° C. and screw speed of 200 rpm. The extrudates were shaped into tablets in a downstream processing step. The tablets were collected and stored in high density polyethylene (HDPE) bottles.

| | % w/w | |
|---|---|---|
| Ingredient | F-3 | F-4 |
| Propranolol Ion Exchange Resin Complex | 50 | 50 |
| Hydroxypropylcellulose (I) (M.W. 370,000) | 26.25 | 8.75 |
| Hydroxypropylcellulose (II) (M.W. 80,000) | 8.75 | 26.25 |
| Polyethylene glycol (M.W. 400) | 15 | 15 |
| Total | 100 | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given in the table below:

| Time | % Released | |
|---|---|---|
| (h) | F-3 | F-4 |
| 1 | 7 | 15 |
| 2 | 14 | 30 |
| 4 | 28 | 59 |
| 6 | 40 | 74 |
| 8 | 49 | 84 |

Extraction Studies

Extraction studies were conducted on the tablets in different solvents using a wrist action shaker at a speed of 416 rpm and 18° angle. Samples were withdrawn at 15 minute and 60 minute time intervals and drug release was measured using a UV-spectrophotometer. The extraction results are given below:

| | Extraction of Intact Tablets % Released | | | |
|---|---|---|---|---|
| Extraction | F-3 | | F-4 | |
| Solvent | 15 min | 60 min | 15 min | 60 min |
| Methanol | 0.9 | 1.9 | 1.6 | 3.4 |
| Water | 0.1 | 0.2 | 0.2 | 0.4 |
| 0.1N HCl | 1.0 | 1.4 | 1.1 | 1.5 |
| Ethanol 40% | 0.3 | 0.5 | 0.3 | 0.7 |
| 0.1N NaOH | 1.8 | 2.1 | 2.2 | 2.2 |
| Ethanol 96% | 0.3 | 1.0 | 0.8 | 1.6 |
| Isopropanol | 0.3 | 0.8 | 0.3 | 0.6 |
| Ethylacetate | 0.3 | 0.7 | 0.3 | 0.6 |

The data demonstrates that the invention permits the development of different Propranolol-ion exchange formulations that have different dissolution profiles and at the same time provide similar tamper resistant properties as demonstrated by the low level of extractability of the therapeutic agent from the tablets.

Example 9

Propranolol-Ion Exchange Tablet Formulations with an Erosion Enhancer

Two different Propranolol-ion exchange complex formulations (F-5 and F-6) containing an erosion enhancer were blended and fed into a 16 mm twin screw extruder and extruded at processing temperatures of 100° C. and screw speed of 200 rpm. The extrudates were shaped into tablets in a downstream processing step. The tablets were collected and stored in high density polyethylene (HDPE) bottles.

| | % w/w | |
|---|---|---|
| Ingredient | F-5 | F-6 |
| Propranolol Ion Exchange Resin Complex | 50 | 50 |
| Hydroxypropylcellulose (I) (M.W. 370,000) | 18.4 | 15.75 |
| Hydroxypropylcellulose (II) (M.W. 80,000) | 6.1 | 5.25 |
| Polyethylenoxide (M.W. 200,000) | 10.5 | 14 |
| Polyethylene glycol (M.W. 400) | 15 | 15 |
| Total | 100 | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given below:

| Time | % Released | |
|---|---|---|
| (h) | F-5 | F-6 |
| 1 | 12 | 12 |
| 2 | 22 | 25 |
| 4 | 39 | 47 |

-continued

| Time (h) | % Released | |
|---|---|---|
| | F-5 | F-6 |
| 6 | 50 | 64 |
| 8 | 58 | 73 |

Extraction Studies

Extraction studies were conducted on intact tablets in different solvents using a wrist action shaker at a speed of 416 rpm and 18° angle. Samples were withdrawn at 15 minutes and 60 minutes, and drug release was measured using a UV-spectrophotometer. The results are given below:

| | Extraction of Intact Tablets % Released | | | |
|---|---|---|---|---|
| Extraction | F-5 | | F-6 | |
| Solvent | 15 min | 60 min | 15 min | 60 min |
| Methanol | 0.5 | 1.6 | 1.1 | 2.8 |
| Water | 0.1 | 0.2 | 0.2 | 0.4 |
| 0.1N HCl | 0.9 | 1.3 | 1.5 | 1.9 |
| Ethanol 40% | 0.2 | 0.5 | 0.4 | 0.8 |
| 0.1N NaOH | 2.5 | 2.1 | 3.1 | 2.6 |
| Ethanol 96% | 0.3 | 0.7 | 0.5 | 1.1 |
| Isopropanol | 0.3 | 0.5 | 0.4 | 0.9 |
| Ethylacetate | 0.3 | 0.5 | 0.2 | 0.4 |

The above examples illustrate that release profiles of dosage forms can be modified using erosion enhancers without compromising the tamper resistance properties of the dosage forms.

Example 10

Propranolol-Ion Exchange Tablet Formulations with a Viscosity Enhancer

A mixture of Propranolol ion exchange resin complex, hydroxypropylcellulose (I), hydroxypropylcellulose (II), polyethylene oxide, polyethylene glycol and silicon dioxide were blended and fed into a 16 mm twin screw extruder and extruded at extrusion temperatures of 140° C. and a screw speed of 200 rpm. The extrudate was shaped into tablets downstream. The tablets were collected and stored in high density polyethylene (HDPE) bottles.

| Ingredient | % w/w |
|---|---|
| Propranolol Ion Exchange Resin Complex | 50 |
| Hydroxypropylcellulose (I) (M.W. 370,000) | 8.6 |
| Hydroxypropylcellulose (II) (M.W. 80,000) | 26.1 |
| Polyethylene Oxide (M.W. 4,000,000) | 8.6 |
| Polyethylene glycol (M.W. 400) | 4.8 |
| Silicon dioxide | 1.9 |
| Total | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given below:

| Time (h) | % Released |
|---|---|
| 1 | 9 |
| 2 | 19 |
| 3 | 29 |
| 4 | 38 |
| 5 | 46 |
| 6 | 55 |
| 7 | 61 |
| 8 | 65 |

Extraction Studies

Extraction studies were conducted on the tablets in different solvents using a wrist action shaker at a speed of 416 rpm and 18° angle. Samples were withdrawn at 15 minute and 60 minute time intervals and drug release was measured using a UV-spectrophotometer. The extraction results are given below:

| | Extraction of Intact Tablets | |
|---|---|---|
| Extraction | % Released | |
| Solvent | 15 min | 60 min |
| Methanol | 2.0 | 3.4 |
| Water | 0.3 | 0.5 |
| 0.1N HCl | 1.4 | 2.0 |
| Ethanol 40% | 0.4 | 0.8 |
| 0.1N NaOH | 2.4 | 2.9 |
| Ethanol 96% | 0.7 | 1.4 |
| Isopropanol | 0.6 | 0.8 |
| Ethylacetate | 0.3 | 0.5 |

The data demonstrates that the invention permits the development of Propranolol-ion exchange formulations that contain viscosity enhancing polymer and at the same time provide similar tamper resistant properties as demonstrated by the low level of extractability of the therapeutic agent from the tablets.

What is claimed is:

1. An extended release tamper-resistant dosage form, comprising:
   at least one therapeutic agent;
   at least one substrate;
   at least one thermoplastic polymer, and
   at least one pharmaceutical additive, wherein
   the at least one therapeutic agent and the at least one substrate form a therapeutic agent-substrate complex, wherein the complex is prepared using a reactive extrusion process that results in the formation of complex particles,
   the at least one thermoplastic polymer and the at least one pharmaceutical additive form a thermo-formable matrix, and
   the therapeutic agent-substrate complex is embedded in the thermo-formable matrix, wherein the complex is embedded in the matrix using a hot melt extrusion process.

2. The dosage form of claim 1, wherein the form is a modified release tablet.

3. The dosage form of claim 1, wherein the form is modified release multiparticulates.

4. The dosage form of claim 1, wherein the at least one therapeutic agent is selected from the group consisting of a narcotic opioid, a CNS depressant, sedative/hypnotics, a stimulant, and a decongestant.

5. The dosage form of claim 4, wherein the narcotic opioid is selected from the group consisting of alfenatil, allylprodine, alphaprodine, anileridine, apomorphine, apocodeine, benzylmorphine, benzitramide, buprenorphine, butorphanol, clonitrazene, codeine, codeine methylbromide, codeine phosphate, codeine sulfate, cyclazocine, cyclorphen, cyprenorphine, desmorphine, dextromoramide, dezocine, diamromide, dihydrocodeine, dihydrocodeinone, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, hydrocodone, hydrocodone barbiturate, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, morphine derivatives, myrophine, nalbuphine, narceine, nicomorphine, norlevorphanol, normethadone, nalorphine, normorphine, norpipanol, ohmefentanyl, opium, oxycodone, oxymorphone, papaverum, pentazocine, phenadoxone, phenomorphan, phenazocine, phenoperidine, pheoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, naloxonazine, trindole, naltrindole isothiocyanate, naltriben, norbinaltorphimine, funaltrexmine, and salts or esters of any of the opioids, and mixtures thereof.

6. The dosage form of claim 4, wherein the CNS depressant, sedative or hypnotic is selected from the group consisting of acecabromal, bomisovalum, capruide, cabromal, ectylurea, chlorhexadol, ethcholorvynol, meparfynol, tetrapentylalcohol, butoctamide, diethylbromoacetamide, ibrotamide, isovarleryl diethylamide, niaprazine, triacetamide, trimetozine, zolpidem, zopiclone, allobarbital, amobarbital, aprobarbital, barbital, brallabarbital, butabarbital sodium, butabarbital, butallylonal, buthetal, carbubarb, cyclobarbital, cyclopentobarbital, enallylpropymal, 5-ethyl-5-(1-piperidyl)barbituric acid, 5-furfuryl-5-isopropylbarbituric acid, heptabarbital, hexethal sodium, hexobarbital, mephobarbital, methitural, narcobarbital, nealbarbital, pentobarbital sodium, phenallylmal, phenobarbital, phenobarbital sodium, phenylmethylbarbituric acid, probarbital, propallylonal, proxibarbal, reposal, secobarbital sodium, thiopental, talbutal, tetrabarbital, thiobarbital, thiamylal, vinbarbital sodium, and vinylbital, benzodiazepine derivatives such as alprazolam, brotizolam, clorazepate, chlordiazepoxide, clonazepam, diazepam, doxefazepam, estazolam, flunitrazepam, flurazepam, haloxazolam, lorazepam, loprazolam, lormetazepam, nitrazepam, quazepam, temazepam, and triazolam; carbamates such as amylcarbamate, ethinamate, hexaprypymate, meparfynol carbamate, novonal and trichlorourethan; chloral derivatives such as carbochloral, chloral betaine, chloral formamide, chloral hydrate, chloralantipyrine, dichloralphenazone, pentaerithriol chloral and triclofos; piperidinediones such as gluthemide, methylprylon, piperidione, taglutimide, thalidomide; quinazolone derivatives such as etaqualone, mecloquanone, and methaqualone; and others such as acetal, acetophenone, aldol, ammonium valerate, amphenidone, d-bornyl-a- bromoisovalerate, d-bornylisovalerate, calcium 2-ethylbutanoate, carfinate, a-chlorolose, clomethiazole, cypripedium, doxylamine, etodroxizine, etomidate, fenadiazole, homofenazine, hydrobromic acid, mecloxamine, methyl valerate, opium, paraldehyde, perlapine, propiomazine, rimazafone, sodium oxybate, sulfomethylmethane and sulfonmethane and mixtures thereof.

7. The dosage form of claim 4 wherein the stimulant is selected from the group consisting of amphethamine, dextroamphethamine, levoamphetamine, methamphetamine, methylphenidate, phenmetrazine, modatinil, avafinil, armodafinil, and ampalimes; cannabinoids such as tetrahydro-cannabinol, nabilone; ketamine, tiletamine, dextromethorphan, ibogaine, dixocilpine, androisoxazole, androstenediol, bolandiiol, clostebol, ethylesternol, formyldienolone, 4-hydroxy-19-nortestosterone, methandriol, methenolone, methyltrienolone, nandrolone, nandrolone deconate, nandrolone p-hexyloxyphenylpropionate, nandrolone phenpropionate, norbolethone, oxymestrone, pizotyline, quinbolone, stenbolone and trenbolone; anorexics such as aminorex, amphecloral, amphethamine, benzaphetamine, chlorphentermine, clobenzorex, cloforex, clortermine, cyclexedrine, dextroamphetamine sulfate, diethylpropion, diphemethoxidine, n-ethylamphetamine, fenbutrazate, fenfluramine, fenproporex, furfurylmethylamphetamine, methamphetamine, levophacetoperate, mazindol, mefenorex, metamfeproamone, methamphetamine, norpseudoephedrine, phendimetrazine, phendimetrazine trtrate, phenmetrazine, phentermine, phenylpropanolamine hydrochloride and picilorex, and mixtures thereof.

8. The dosage form of claim 4 wherein the decongestant is selected from the group consisting of pseudoephedrine, ephedrine, Levo-methamphetamine phenylpropanolamine, propylhexedrine and Synephrine, and mixtures thereof.

9. The dosage form of claim 1, wherein the at least one therapeutic agent is selected from group consisting of atenolol, albendazole, alendronate, alprostadil, allopurinol, amlexanox, anagrelide, aminophylline, alitretinoin, amodiaquine, astemizole, atovaquone, aztreonam, atorvastatin, azlocillin, baclofen, benazepril, benzonatate, bitolterol mesylate, brompheniramine, cabergoline, carisoprodol, celecoxib, cefpiramide, chlorothiazide, chlormezanone, cimetidine, cetirizine, cefotaxime, ciprofloxacin, cephalexin, chloroquine, clomocycline, cyclobenzaprine, cyproheptadine, cyproheptadine, cefmenoxime, cyclophosphamide, ciclopirox, cladribine, chlorpheniramine, chlorzoxazone, clemastine, clofarabine, cytarabine, dacarbazine, dantrolene, daunorubicin, dexamethasone, diclofenac, diethylcarbamazine, diphenhydramine, diphenylpyraline, disopyramide, diltiazem, dopamine, dofetilide, doxazocin, enoxacin, epirubicin, eplerenone, erlotinib, ertapenem, etoposide, exemestane, ezetimibe, fexofenadine, flucloxacillin, fulvestrant, fenofibrate, fenoprofen, fenoldopam, fluocinonide, flunisolide, fluorouracil, gefitinib, gemcitabine, grepafloxacin, guaifenesin, halofantrine, ibuprofen, ibandronate, ipratropium, irinotecan, isosorbide mononitrate, ipratropium, ivermectin, ketoconazole, ketoprofen, ketorolac, levamisole, letrozole, levosimendan, levofloxacin, lovastatin, loratadine, lymecycline, loracarbef, lisuride, meclofenamate, mefloquine, meloxicam, methocarbamol, methylbromide, metolazone, methyldopa, methdilazine, mequitazine, mitotane, mivacurium, moxifloxacin, mometasone, midodrine, milrinone, nabumetone, naproxen, nifedipine, nilutamide, nedocromil, omeprazole, olmesartan, oxaliplatin, oxamniquine; orphenadrine, pantoprazole ,pefloxacin, pentamidine, penicillamine, pemetrexed, perhexiline, phenylbutazone, pipobroman, piroxicam, propranolol, phentermine, phentolamine, piperacillin, piperazine, primaquine, piroxicam, pivoxil, praziquantel, probenecid, porfimer, propafenone, prednisolone, proguanil, pyrimethamine, quinine, quinidine, ranolazine, remikiren, rofecoxib, salmeterol, sulfanilamide, sulfadiazine, suprofen, sulfinpyrazone, tenoxicam, triamterene, tolmetin, toremifene, tolazoline,tamoxifen, teniposide, theophylline, terbutaline, terfenadine, thioguanine, tolmetin, trimetrexate, triprolidine, trovafloxacin, verapamil, valsartan, vinorelbine, valrubicin, vincristine, valdecoxib and mixtures thereof.

10. The dosage form of claim 1, wherein the at least one substrate is selected from the group consisting of a polyelectrolyte, a fatty acid, a pharmacologically-inert organic component of prodrugs, an inorganic adsorbent, an organic acids and an inclusion compound.

11. The dosage form of claim 10, wherein the polyelectrolyte is selected from the group consisting of a natural polyelectrolyte, a chemically modified polyelectrolyte, and a synthetic polyelectrolyte.

12. The dosage form of claim 11, wherein the natural polyelectrolyte is selected from the group consisting of nucleic acids, poly (L-lysine), poly (L-glutamic acid), carrageenan, alginates, and hyaluronic acid, and mixtures thereof.

13. The dosage form of claim 11 wherein the chemically modified polyelectrolyte is selected from the group consisting of pectin, chitosan (deacetylation of chitin), cellulose-based, starch-based and dextran-based polymers and mixtures thereof.

14. The dosage form of claim 11, wherein the synthetic polyelectrolyte is selected from group consisting of poly (vinylbenzyl trialkyl ammonium), poly (4-vinyl-N-alkyl-pyridimiun), poly (acryloyl-oxyalkyl-trialkyl ammonium), poly (acryamidoalkyl-trialkyl ammonium), poly (diallydimethyl-ammonium), poly (acrylic or methacrylic acid), and poly (itaconic acid) and maleic acid/ diallyamine copolymer, carbopols, crosscarmellose, ion exchange resin, and mixtures of.

15. The dosage form of claim 14, wherein the ion exchange resin is selected from the group consisting of a sulfonated copolymer of styrene and divinylbenzene, a carboxylate copolymer of styrene and divinylbenzene, a copolymer of styrene and divinylbenzene containing quaternary ammonium groups.

16. The dosage form of claim 15, wherein the ion exchange resin is selected from the group consisting of sodium salt of styrene divinylbenzene sulfonate copolymer, sodium salt of styrene divinylbenzene sulfonate copolymer, methacrylic acid divinylbenzene carboxylate copolymer, sodium salt of styrene divinylbenzene sulfonate copolymer, sulfonate of styrene and divinylbenzene copolymer consisting of 2% cross linking, sulfonate of styrene and divinylbenzene copolymer consisting of 4% cross linking, sulfonate of styrene and divinylbenzene copolymer consisting of 8% cross linking, styrene and divinylbenzene with quaternary ammonium functional group, crosslinked polyacrylic polymer with carboxylic acid functional group having particle size 45% larger than 75 micron, crosslinked polyacrylic polymer with carboxylic acid functional group having particle size 45% larger than 75 micron, potassium salt of crosslinked polyacrylic polymer having particle size 70% larger than 75 microns, crosslinked polyacrylic polymer with carboxylic acid functional group having particle size 30% larger than 75 microns), crosslinked polyacrylic polymer with carboxylic acid functional group, potassium salt of crosslinked polyacrylic polymer with carboxylic acid functional group, and crosslinked polyacrylic polymer with carboxylic acid functional group and mixtures thereof.

17. The dosage form of claim 10, wherein the fatty acid is selected from the group consisting of arachidonic acid, capric acid, caprylic acid, dihomo-γ-linoleic acid, docesenoic acid, docosatetraenoic acid, docosohexaconic acid, docosopentanoic acid, eicosapentanoic acid, gondoic acid, lauric acid, linoleic acid, α-linoleic acid, 6-linoleic acid, myristic acid, nervonic acid, oleic acid, oleostearic acid, palmitic acid, palmitoleic acid, stearic acid, and vaccenic acid and mixtures thereof.

18. The dosage form of claim 10 wherein the pharmacologically-inert organic component of prodrugs is selected from the group consisting of amides and esters.

19. The dosage form of claim 10 wherein the inorganic adsorbent is selected from the group consisting of silicon dioxide, aluminum silicate, attapulgite, bentonite, calcium silicate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, zeolite, and zirconium silicate and mixtures thereof.

20. The dosage form of claim 10, wherein the organic acid is selected from the group consisting of acetates, besylates, tartrates, citrates, maleates, succinates, fumarates, adipiates, and oxalates and mixtures thereof.

21. The dosage form of claim 10 wherein the inclusion compound is selected from the group consisting of α-cyclodextrin, β-cyclodextrin and γ-cyclodextrin.

22. The dosage form of claim 1, wherein the at least one thermoplastic polymer is selected from the group consisting of a cellulose derivative, a vinyl derivative, an acrylate, a polyoxide and a polyglycol.

23. The dosage form of claim 22, wherein the cellulose derivative is selected from the group consisting of hydroxylpropyl cellulose, hydroxylpropyl methylcellulose, hydroxyethyl cellulose, and methylcellulose, and mixtures thereof.

24. The dosage form of claim 22 wherein the vinyl derivative is selected from the group consisting of polyvinyl pyrrolidone, polyvinyl acetate and polyvinyl alcohol, and mixtures thereof.

25. The dosage form of claim 22 wherein the acrylate is selected from a group consisting of butyl/methyl methacrylate-dimethylaminoethylmethacrylate copolymer.

26. The dosage form of claim 22, wherein the polyglycol is selected from a group consisting of polyethylene glycol, polyethylene oxide, polypropylene glycol and polyvinyl caprolactam-polyvinyl acetate-polyethylene glycol.

27. The dosage form of claim 1, wherein the at least one pharmaceutical additive is selected from the group consisting of a plasticizer, a wax, a surfactant, an inorganic filler, an anti-adherent, an erosion enhancer, and a stabilizer.

28. The dosage form of claim 27, wherein the plasticizer is selected from the group consisting of dibutyl sebacate, glycerol, polyethylene glycol, propylene glycol, triacetin, tributyl citrate, and triethyl citrate and mixtures thereof.

29. The dosage form of claim 27, wherein the wax is selected from the group consisting of bee's wax, candilila wax, carnuba wax, and paraffin wax and mixtures thereof.

30. The dosage form of claim 27, wherein the surfactant is selected from the group consisting of alkyl benzene sulfones, alkyl sulfates, ether carboxylates, glycerol/propylene glycol fatty acid esters, hexadecyl triammonium bromide, hydroxylated lecithin, lauryl carnitine, lower alcohol-fatty acid esters, mono-/di-glycerides, phospholipid extracted from egg, polyethylene glycol alkyl ethers, polyethylene glycol-fatty acid monoesters, polyethylene glycol-glycerol esters, polyethylene glycol phenols, polyethylene glycol-sorbitan fatty acid esters, polyglyceride fatty acids, polyoxyethylene-polyoxypropylene block copolymers, propylene glycol-fatty acid esters, sodium cholate, sodium lauryl sulfate, sodium palmitate, sodium taurocholate, sorbitan-fatty acid esters, sterol and sterol derivatives, sugar esters, and mixtures thereof.

31. The dosage form of claim 27, wherein the inorganic adsorbent is selected from the group consisting of aluminum silicate, attapulgite, bentonite, calcium silicate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, zeolite, and zirconium silicate and mixtures thereof.

32. The dosage form of claim 27, wherein the anti-adherent is selected from the group consisting of calcium carbonate, dicalcium phosphate, kaolin, talc, and titanium dioxide, and mixtures thereof.

33. The dosage form of claim 27, wherein the erosion enhancer is selected from the group consisting of a low molecular weight polymer, a polyol and a surface active agent, and mixtures thereof.

34. The dosage form of claim 33, wherein the low molecular weight polymer is selected from the group consisting of hydroxypropyl cellulose, hydroxypropylmethyl cellulose, polyethylene oxide, polyvinyl pyrollidone and mixtures thereof.

35. The dosage form of claim 33, wherein the polyol is selected from the group consisting of mannitol, malitol, sorbitol, xylytol and lactose, and mixtures thereof.

36. The dosage form of claim 33, wherein the surface active agent is selected from the group consisting of sodium lauryl sulfate, Polysorbate 80, and chremophor, and mixtures thereof.

37. The dosage form of claim 27 wherein the stabilizer is selected from the group consisting of an antioxidant, a buffering agent, and mixtures thereof.

38. The dosage form of claim 37, wherein the antioxidant is selected from the group consisting of butylhydroxytoulene, butylhydroxyanisole, propyl gallate, ascorbic acid, vitamin E-TPGS, and mixtures thereof.

39. The dosage form of claim 37 wherein the buffering agent is selected from the group consisting of phosphates, citrates, acetates, oxides, carbonates, and mixtures thereof.

40. A process of preparing a tamper-resistant dosage form, comprising the steps of:
  (1) blending at least one therapeutic agent and at least one substrate in a therapeutic agent-to-substrate ratio between 1:10 to 10:1;
  (2) reacting the at least one therapeutic agent and the at least one substrate to form a therapeutic agent-substrate complex;
  (3) forming a thermo-formable matrix blend with at least one thermoplastic polymer and optionally at least one pharmaceutical additive;
  (4) mixing the therapeutic agent-substrate complex and the thermo-formable matrix blend in a ratio between 1:20 to 20:1;
  (5) granulating the therapeutic agent-substrate complex and the thermo-formable matrix blend to form the tamper-resistant dosage form in which the therapeutic agent-substrate complex is embedded in the thermo-formable matrix; and
  (6) shaping the tamper-resistant dosage form into one of an immediate release or modified release tablet form and an immediate release or modified release multiparticulate form.

41. The process of claim 40, wherein the reacting step of (2) is carried out by a reactive extrusion process.

42. The process of claim 40, wherein the granulating step of (5) is carried out by a hot melt extrusion process.

43. The process of claim 40, wherein the granulating step of (5) is optionally carried out by a wet granulation process.

44. The process of claim 40, wherein the granulating step of (5) is optionally carried out by a dry granulation process.

* * * * *